(12) United States Patent
Benditt et al.

(10) Patent No.: US 7,899,526 B2
(45) Date of Patent: Mar. 1, 2011

(54) PORTABLE DEVICE FOR MONITORING ELECTROCARDIOGRAPHIC SIGNALS AND INDICES OF BLOOD FLOW

(75) Inventors: David G. Benditt, Edina, MN (US); Robert F. Patterson, Minneapolis, MN (US); Keith G. Lurie, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 11/127,055

(22) Filed: May 10, 2005

(65) Prior Publication Data

US 2005/0267381 A1 Dec. 1, 2005

Related U.S. Application Data

(60) Provisional application No. 60/569,551, filed on May 10, 2004.

(51) Int. Cl.
*A61B 5/05* (2006.01)
*A61B 5/02* (2006.01)

(52) U.S. Cl. .......... 600/547; 600/481; 600/504; 600/506

(58) Field of Classification Search ............... 600/547, 600/481–528; 607/8
See application file for complete search history.

(56) References Cited

U.S. PATENT DOCUMENTS

| | | | |
|---|---|---|---|
| 4,774,950 A | 10/1988 | Cohen | |
| 4,846,191 A | 7/1989 | Brockway et al. | |
| 4,899,751 A | 2/1990 | Cohen | |
| 5,269,301 A | 12/1993 | Cohen | |
| 5,431,685 A | 7/1995 | Alt | |
| 5,441,525 A | 8/1995 | Shelton et al. | |
| 5,487,760 A | 1/1996 | Villafana | |
| 5,865,749 A | 2/1999 | Doten et al. | |
| 5,913,879 A | 6/1999 | Ferek-Petri et al. | |
| 5,957,861 A * | 9/1999 | Combs et al. | 600/547 |
| 6,033,366 A | 3/2000 | Brockway et al. | |
| 6,259,936 B1 | 7/2001 | Boggett et al. | |
| 6,351,670 B1 | 2/2002 | Kroll | |
| 6,477,406 B1 | 11/2002 | Turcott | |

(Continued)

FOREIGN PATENT DOCUMENTS

WO WO98/51212 11/1998

(Continued)

OTHER PUBLICATIONS

International Search Report of Jun. 13, 2006 for PCT application PCT/US05/16396.

(Continued)

*Primary Examiner* — Jeffrey G Hoekstra
(74) *Attorney, Agent, or Firm* — Fish & Richardson P.C.

(57) ABSTRACT

Embodiments of the present invention are directed to a physiological monitoring device which is configured to record signals that reflect blood flow and/or blood pressure, and which may also record ECG signals. In one embodiment, a portable monitoring device comprises a plurality of impedance electrodes configured to be coupled to a patient's body and to generate an AC current with an electrical field to detect local electrical impedance of a portion of the patient's body encompassed by the electrical field, the local electrical impedance being a surrogate measure of local blood flow of the portion of the patient's body. At least a portion of the portable monitoring device is configured to be insertable subcutaneously into the patient's body.

18 Claims, 3 Drawing Sheets

U.S. PATENT DOCUMENTS

| | | |
|---|---|---|
| 6,480,733 B1 | 11/2002 | Turcott |
| 6,491,639 B1 | 12/2002 | Turcott |
| 6,510,342 B1 | 1/2003 | Park et al. |
| 6,512,949 B1 * | 1/2003 | Combs et al. .................. 600/547 |
| 6,527,729 B1 | 3/2003 | Turcott |
| 6,561,948 B2 | 5/2003 | Markyvech et al. |
| 6,561,986 B2 * | 5/2003 | Baura et al. .................. 600/526 |
| 6,575,912 B1 | 6/2003 | Turcott |
| 6,575,914 B2 | 6/2003 | Rock et al. |
| 6,600,949 B1 | 7/2003 | Turcott |
| 6,616,624 B1 | 9/2003 | Kieval |
| 6,625,492 B2 | 9/2003 | Florio et al. |
| 6,647,295 B2 | 11/2003 | Florio et al. |
| 6,662,047 B2 | 12/2003 | Sorensen et al. |
| 7,097,618 B1 | 8/2006 | Benditt et al. |
| 2002/0072731 A1 | 6/2002 | Doten et al. |
| 2002/0107559 A1 | 8/2002 | Sanders et al. |
| 2003/0229380 A1 | 12/2003 | Adams et al. |

FOREIGN PATENT DOCUMENTS

| | | |
|---|---|---|
| WO | WO 2005/110051 A2 | 11/2005 |

OTHER PUBLICATIONS

Written Opinion of Jun. 13, 2006 for PCT application PCT/US05/16396.

International Preliminary Report on Patentability of Nov. 14, 2006 for PCT application PCT/US05/16396.

Priebe, Hans-Joachim, "Vasoactive Drugs", IARS 2004 Review Course Lectures, pp. 64-70.

Moya et al., "Mechanism of Syncope in Patients With Isolated Syncope and in Patients With Tilt-Positive Syncope", *Circulation* 2001; 104; 1261-1267.

* cited by examiner

PORTABLE DEVICE FOR MONITORING ELECTROCARDIOGRAPHIC SIGNALS AND INDICES OF BLOOD FLOW

CROSS-REFERENCES TO RELATED APPLICATIONS

This application is based on and claims the benefit of U.S. Provisional Patent Application No. 60/569,551, filed May 10, 2004, the entire disclosure of which is incorporated herein by reference.

BACKGROUND OF THE INVENTION

The present invention relates to diagnostic monitoring systems and, more particularly, to a portable diagnostic monitoring system for assessing cardiovascular hemodynamic state during the setting of a normal or abnormal heart rhythm. Advantageously, the monitoring system is capable of detecting abnormalities of blood pressure and/or flow.

Changes in cardiac output or blood pressure may be of value in diagnosis and management chronic and/or recurring disease states (e.g., congestive heart failure, hypertension, syncope). Currently, such measurements require invasive intravascular catheters with attached sensors (e.g., pressure, oxygen saturation) or an intra-arterial cannula.

Devices employing the technique of impedance plethysmography (commonly known as Impedance Cardiographs (ICG) when applied to the thorax) have been developed which are external to the body and can provide a surrogate marker of pulsatile blood volume changes and/or surrogate measure of blood flow by detection of changes in bioelectrical impedance (BEI). Typically, these devices use band or spot electrodes around the ends of the thorax and measure change in chest impedance due to altered vascular volumes corresponding to cardiac activity. Current is transmitted through the chest and seeks the path of least resistance, i.e., the blood filled aorta. With each heartbeat, the blood volume and velocity of the aorta change. Impedance plethysmography measures the corresponding change in impedance and calculates the hemodynamic parameters.

BRIEF SUMMARY OF THE INVENTION

The invention addresses the medical problem of evaluating the hemodynamic impact of a cardiac arrhythmia or suspected cardiac arrhythmia in free-living individuals. The objective may be accomplished by correlating electrocardiographic (ECG) recordings with surrogate measurements of blood pressure and/or blood flow obtained from a portable (wearable or insertable) cardiac monitor. In essence, for instances in which there is suspicion that heart rhythm disturbances are causing symptoms (e.g., dizziness, syncope, or weakness), the ability to correlate a documented arrhythmia with its hemodynamic effect will allow the physician to better assess the true impact of the arrhythmia on the patient. Additionally, some patients may exhibit hemodynamic disturbances (e.g., abrupt hypotension) without concomitant arrhythmia. Examples include certain vasodepressor faints in which the main problem is dilation of arterial blood vessels causing a fall in blood pressure, or in some individuals in association with movement from supine or seated to upright posture (e.g., orthostatic hypotension and/or orthostatic faints). In these conditions the heart rhythm may remain normal, or only relatively minor abnormalities are recorded and the heart rate may remain within the normal range; nonetheless, the blood pressure becomes abnormally low. Currently, these latter conditions are difficult to document in free-living individuals as they occur unpredictably over time, and at present there is no available portable monitor systems which can document both ECG and hemodynamic alterations over relatively long periods (e.g., weeks or months).

Embodiments of the present invention are directed to a physiological monitoring device which is configured to record signals that reflect blood flow and/or blood pressure, and which may also record ECG signals. In an exemplary embodiment, a portable diagnostic monitoring device is capable of detecting abnormal cardiac rhythms and assess their impact on blood flow, as well as detect abnormalities of blood flow that may or may not be associated with an abnormal heart rhythm. An example of clinical use is the evaluation of individuals experiencing syncope (faints) of unknown origin. The monitoring device may be worn on the body surface of the patient. A more practical embodiment of the monitoring device is of a sufficiently small size as to be insertable into the body of the patient using techniques essentially identical to placement of a conventional pacemaker generator. In the exemplary embodiment, intra-vascular access is not utilized, so that the system offers diagnostic capabilities without invading blood vessels to insert sensors. In other embodiments, intravascular or extravascular leads may be used to enhance the diagnostic capability. In yet other embodiments, the monitoring device may be incorporated into a conventional pacemaker or implantable defibrillator (ICD) to enhance the diagnostic capability of those instruments.

In accordance with an aspect of the present invention, a portable monitoring device comprises a plurality of impedance electrodes configured to be coupled to a patient's body and to generate an AC current with an electrical field to detect local electrical impedance of a portion of the patient's body encompassed by the electrical field, the local electrical impedance being a surrogate measure of local blood flow of the portion of the patient's body. At least a portion of the portable monitoring device is configured to be insertable subcutaneously into the patient's body.

In some embodiments, the impedance electrodes are to be placed in close proximity to (e.g., within less than about 5 cm of) a target region of the patient's body to be monitored. The impedance electrodes are configured to detect local electrical impedance near an artery in the patient's body. The impedance electrodes include two electrodes that are spaced from one another in a direction generally parallel to or transversely across the artery. A temperature sensor may also be used in this device to aid in assessing local blood flow and/or monitoring for recurring disease states that may cause fever. The temperature sensor is configured to measure local tissue temperature of the patient's body near the temperature sensor. A plurality of ECG electrodes are configured to be coupled to the patient's body. A telemetry component is configured to communicate telemetrically with an external device. A warning component, which may be activated or deactivated by an external telemetry link, provides warning based on the detected information. The impedance electrodes are can-mounted surface electrodes. Auxiliary leads are coupled with the impedance electrodes.

In specific embodiments, a memory is configured to store physiological information obtained by detecting the local electrical impedance by the impedance electrodes. The memory is configured to store physiological data based on instructions delineating criteria for data to be stored. The memory has looping memory capability. The memory is configured to store data temporally proximate to an event based on information detected by the impedance electrodes or patient-activated triggering.

In accordance with another aspect of the present invention, a portable monitoring device comprises a plurality of impedance electrodes configured to be coupled to a patient's body and to generate an AC current with an electrical field to detect local electrical impedance of a portion of the patient's body encompassed by the electrical field; a plurality of ECG electrodes configured to be coupled to the patient's body; and a memory configured to store physiological information obtained by detecting the local electrical impedance by the impedance electrodes and by the ECG electrodes.

In some embodiments, the impedance electrodes and the ECG electrodes are can-mounted surface electrodes. Auxiliary leads may also be coupled with at least some of the impedance electrodes and the ECG electrodes.

In accordance with another aspect of the invention, a method of monitoring a patient comprises coupling a plurality of impedance electrodes to a patient's body to generate an AC current with an electrical field to detect local electrical impedance of a portion of the patient's body encompassed by the electrical field, the local electrical impedance being a surrogate measure of local blood flow of the portion of the patient's body; and inserting at least a portion of a portable monitoring device including the impedance electrodes subcutaneously into the patient's body.

In some embodiments, the impedance electrodes are placed in the vicinity (e.g., usually within less than about 5 cm) of a target region of the patient's body to be monitored (e.g., an artery such as the subclavian artery). The impedance electrodes may be applied to a muscle of the patient's body to be monitored. Two of the impedance electrodes may be positioned near an artery and spaced in a direction generally parallel to the artery. Local tissue temperature of the patient's body may also be measured. ECG data of the patient may also be measured. The method may further include transferring information obtained by the impedance electrodes and other sensors (e.g., temperature sensors, ECG electrodes) to an external device disposed outside the patient's body. A warning is generated based on the detected information using pre-determined criteria programmed into the device by the user (e.g., physician). The method further comprises storing physiological information obtained by detecting the local electrical impedance by the impedance electrodes. The information is stored based on instructions delineating criteria for data to be stored. The information is stored proximate to an event based on information detected by the impedance electrodes or patient-activated triggering.

In specific embodiments, the method further comprises coupling auxiliary leads to the impedance electrodes and positioning the auxiliary leads in a target location in the patient's body. The method may further comprise providing the impedance electrodes in an implantable diagnostic device.

A further configuration permits automatic telemetry of information to an external receiver/transmitter for automatic transfer to a distant monitoring station such as by radiowaves, wireless telephony, or direct internet connection.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
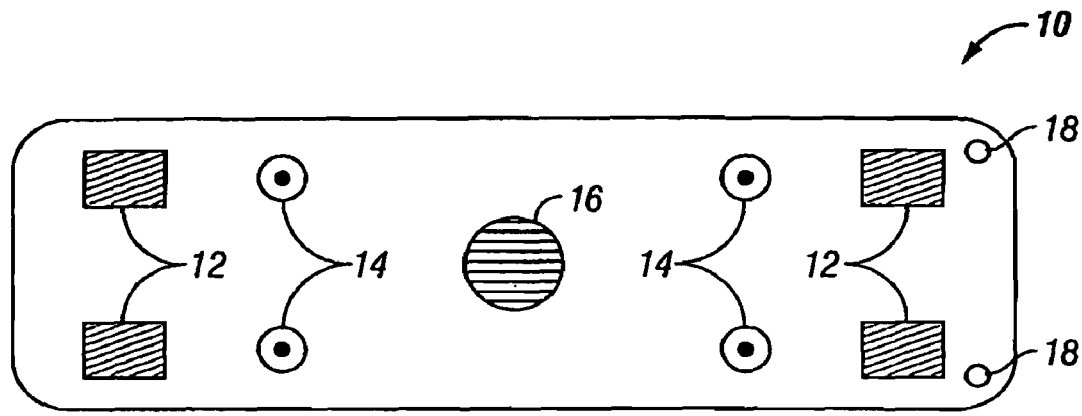
FIG. 1 is a plan view of a portable monitoring device according to an embodiment of the present invention.
Figure 2:
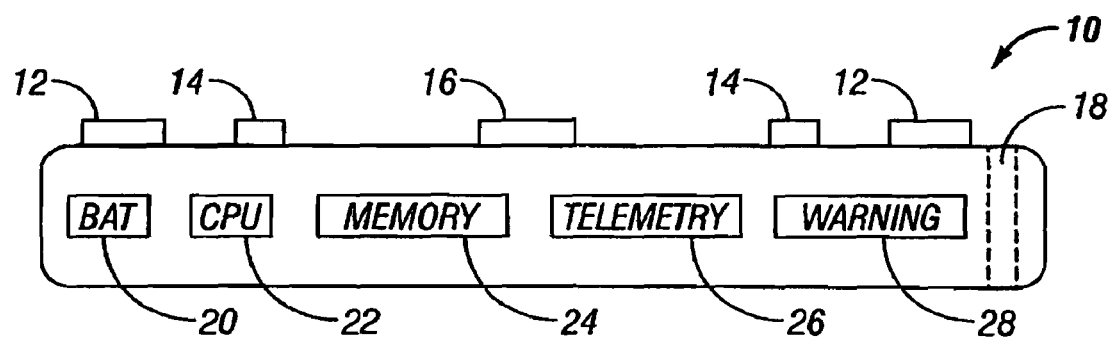
FIG. 2 is an elevational view of the portable monitoring device of FIG. 1.

FIGS. 1 and 2 show a monitoring device 10 which includes a plurality of impedance electrodes 12, a plurality of ECG electrodes 14, a temperature sensor 16, and a plurality of suture ports 18. FIGS. 1 and 2 show four impedance electrodes 12 that are spaced from each other and four ECG electrodes 14 that are spaced from each other, although fewer (e.g., two impedance electrodes and two ECG electrodes) or more electrodes may be used in other embodiments. The use of four impedance electrodes 12 can eliminate electrode interface artifacts and the high electrode tissue impedance. The sensors and electrodes are depicted as protruding from the surface, but they may be flat. In the specific embodiment shown, the impedance electrodes 12, ECG electrodes 14, and temperature sensor 16 are built into the body or can of the monitoring device 10. The monitoring device 10 is desirably a stand-alone, self-powered device with a battery 20, which may be rechargeable. There is no need for intra-cardiac electrodes, although the addition of intra- or extra-cardiac electrodes may be employed to enhance the diagnostic capabilities in alternative embodiments. The monitoring device 10 is compact, typically less than half the size of a conventional modern pacemaker. It is designed to collect, store, and transmits surrogate blood pressure and/or flow data as well as ECG data. Various embodiments may include all or some of the sensors and electrodes depicted.

The impedance electrodes 12 are configured to transmit electrical signals and/or measure the resulting local electrical impedance as it is determined by the signals passing through tissue and/or blood vessels in the vicinity of the impedance electrodes 12, as encompassed by an electrical field of an AC current generated by the impedance electrodes 12. More particularly, the impedance electrodes 12 can measure surrogates of the local blood flow characteristics (e.g., blood flow volume or velocity) of the local tissue zone and, more precisely, the pulsatile blood volume change in the muscle in the local tissue zone being sampled. The impedance electrodes 12 generate an AC current with an electrical field that encompasses the local tissue zone being sampled to measure voltage drop therebetween. The voltage drop depends on the impedance corresponding to the pulsation of blood. The blood flow oscillates over time, and intermittently changes the impedance over time. For instance, the impedance may represent the relative magnitudes of blood flow (increasing or decreasing), or may be a relative measure of the blood flow (volume and/or velocity) with respect to an earlier time. The local impedance change is expected to be proportional to changes in the pulsatile blood volume change in the muscle in the tissue zone being sampled. A minimum of two impedance electrodes 12 are used. Additional impedance electrodes 12 allow different impedance or voltage drop vectors to be generated to provide a better chance of detecting changes in the blood flow characteristics.

Figure 3A:
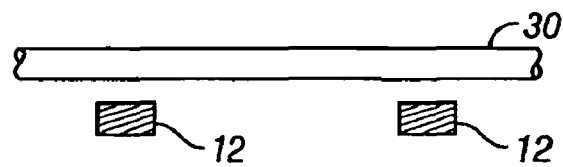
FIGS. 3A-3D are simplified schematic views of the positioning of the impedance electrodes relative to an artery.
Figure 3B:
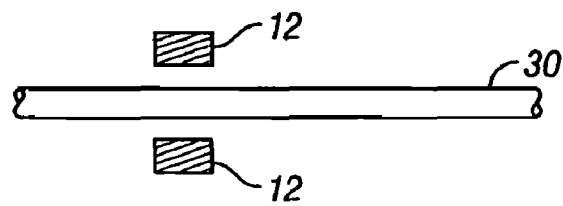
Figure 3C:
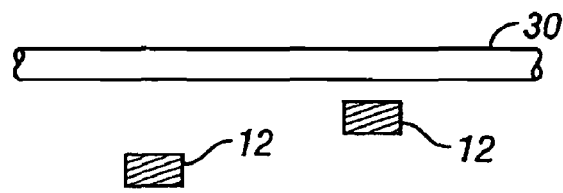
Figure 3D:
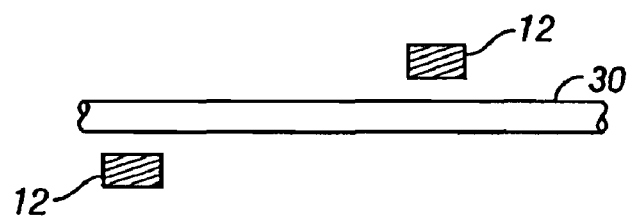

In some embodiments, the impedance electrodes 12 are configured to be disposed near the artery or arteries being monitored, typically separated by less than about 5 cm, more desirably about 3-4 cm. The distance depends on the strength of the electrical field of the AC current being generated, and can increase with an increase in the strength of the electrical field. The artery 30 may be disposed generally parallel to the spacing between two impedance electrodes (e.g., FIG. 3A); the impedance electrodes may be disposed generally transversely across the artery on opposite sides thereof (e.g., FIG. 3B); or the impedance electrodes may be disposed at an angle relative to the artery (e.g., FIG. 3C or 3D). Measurement using the transverse arrangement may be less effective than using the longitudinal or parallel arrangement, since blood resistivity changes with flow, and decreases in the longitudinal direction and increases in the transverse direction due to the lining up of the red cells. The impedance electrodes are described as extra-vascular sensors, but may be positioned within the vascular system (intra-vascular) in other embodiments.

It is noted, however, that the impedance electrodes 12 are configured to be applied over any target region on a patient's body for detecting a surrogate marker of pulsatile blood volume changes or blood flow. The target region may be the muscle of the body or some tissue region. In that case, the impedance electrodes 12 need not be placed in the vicinity of any arteries.

The temperature sensor 16 measures local tissue temperature which may be a surrogate marker for blood pressure and/or blood flow measurement. The sensor 16 can detect flow-related temperature differences. A sensitive recording system is preferably used. For instance, an abrupt local temperature change may reasonably be interpreted as being due to acute changes in local blood flow. Slow temperature changes may reflect environmental factors, or a fever, etc. Rapid temperature changes, albeit of a small magnitude, is most likely related to blood flow alterations.

The ECG electrodes 14 increase the clinical utility of the monitoring device 10 by recording one or more ECG lead vectors. The data collected by the ECG electrodes 14 may be used to correlate with the data collected by the impedance electrodes 12 and/or the temperature sensor 16 to assist physicians in distinguishing whether cardiac arrhythmias are responsible for hypotensive symptoms or other mechanisms are at fault. Other sensors may be used to detect flow change utilizing, for example, laser Doppler techniques (photoplethysmography) or local detection of hemoglobin by reflectance methods.

As seen in FIG. 2, the monitoring device 10 includes a processor 22 and a memory 24 for storing data collected by the electrodes and sensor. The monitoring device 10 may be programmed to collect and process data using the processor 22 and memory 24 as desired by the user and/or manufacturer. The memory 24 may store the data temporarily or permanent. The data may be transmitted to a remote site, such as a memory device worn by the patient or a server elsewhere, after data transfer by a telemetry link with the telemetry component 26. Information may be transmitted via the telemetry component 26 between the device 10 and an external system such as a central monitoring center. Data may be transmitted automatically or after telemetry instruction from an external user such as physician or nurse. The device 10 may be programmed to store all or some of the recorded data based upon downloaded instructions delineating criteria for data storage (e.g., outside upper or lower heart rate boundaries). A warning component 28 such as a buzzer or audible alert may be incorporated in order to warn the patient of an impending problem.

Figure 4:
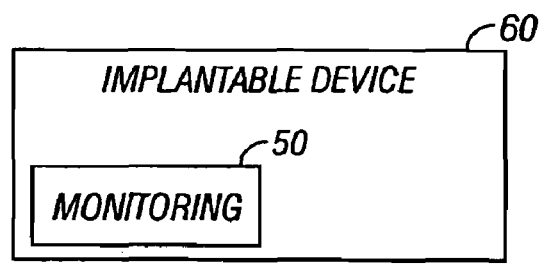
FIG. 4 is a simplified schematic view of a monitoring device incorporated in an implantable device such as a pacemaker or ICD.

In specific embodiments, the monitoring device 10 is inserted into the body of the patient under the skin, more typically under the subcutaneous tissue. For example, the monitoring device 10 may be inserted subcutaneously under the collar bone to be disposed near the subclavian artery. If the monitoring device 10 is inserted to place the impedance electrodes 12 against the pectoralis muscles, a surrogate assessment of skeletal muscle blood flow will be the target to be monitored. An insertable monitoring device is more practical than a wearable one for long term use because it eliminates the need to attach electrodes or the like onto the external skin surface of the patient. In yet another embodiment, the monitoring device 10 may be incorporated into an implantable device such as a cardiac pacemaker, an implantable defibrillator (ICD), or the like to provide additional diagnostic or hemodynamic feedback capability (see, e.g., U.S. Pat. No. 5,441,525). FIG. 4 shows a simplified schematic view of monitoring device components 50 as a part of an implantable device 60.

While FIGS. 1 and 2 show can-mounted surface electrodes, lead-mounted electrodes may be used. Unipolar and/or bipolar signals can be detected. One or more ECG vectors can be provided by the positioning of electrodes on the can or header, or on auxiliary leads designed to be positioned in the extra-vascular tissues, or on intra-vascular or intra-cardiac electrodes. The leads and can may both be inserted under the skin, or either or both the leads and can may be mounted on the body surface.

Figure 5:
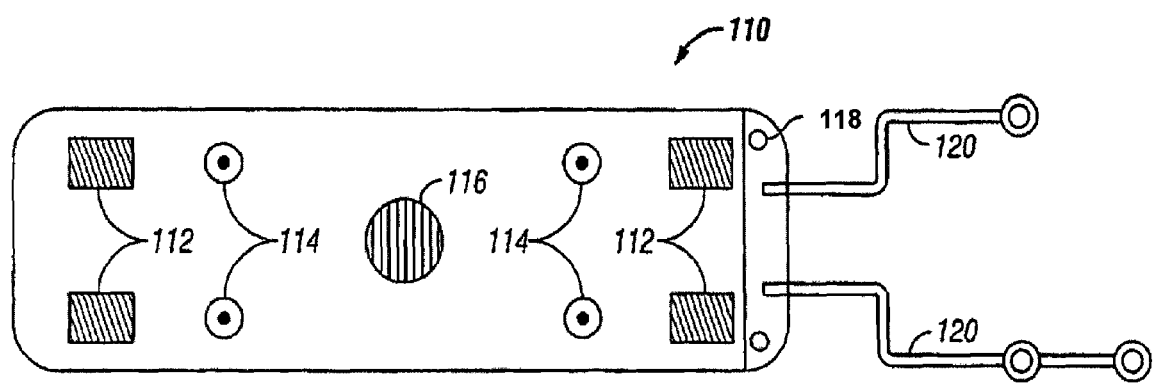
FIG. 5 is a plan view of a portable monitoring device including leads according to another embodiment of the present invention.

FIG. 5 shows another monitoring device 110 having impedance electrodes 112, ECG electrodes 114, a temperature sensor 116, and suture ports 118. Additional leads 120 are provided for remote placement. These auxiliary extra-vascular tissue leads 120 are provided for any of the electrodes 12, 14 and temperature sensor 16 to place them in closer proximity with the desired target(s) to be monitored. A needle or the like can be used to guide the leads 120 and manipulate them subcutaneously to the desired locations. In alternative embodiments, the electrodes, sensors, and/or leads may be detachable rather than fixed to the body of the device.

In specific embodiments, the memory capability of the monitoring device 10 is "looping" (first in, first out) with programmable durations of the "loop" permitting the saving of information prior to automatic or patient-activated triggering of the recordings. Programmability will be such as to permit all or only a subset of detected signals to be stored for subsequent immediate or later transmission to the body surface of the patient, and ultimately to medical personnel for interpretation (e.g., by wireless telephony). For instance, the monitoring device 10 can be programmed to save data temporally proximate certain events (just before and just after), such as an abrupt substantial change in surrogate measures of blood flow (e.g., impedance or temperature).

Figure 6:
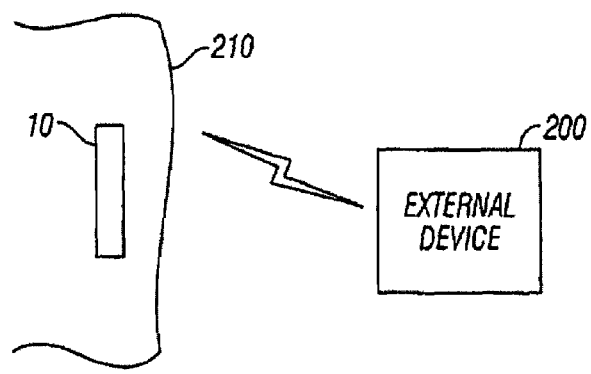
FIG. 6 is a simplified schematic view of an external device for communicating with a monitoring device inserted into a patient.

The patient may be offered a custom-programmed handheld PDA (personal digital assistant) or a similar external device 200, as illustrated in FIG. 6. In FIG. 6, the monitoring device is inserted under the skin 210 of the patient. The patient may use the external device 200 to instruct the implanted or inserted monitoring device 10 to collect and/or transmit data at such times as the patient feels appropriate (e.g., real-time records recorded during a symptom event or looped records saved by transmitted after symptoms). The monitoring device 10 may also be programmed to retain and transmit data automatically when certain predetermined physiological boundaries are exceeded (e.g., blood flow surrogate or heart rate above or below preset limits). Communication may be automatic or initiated by an external user such as a physician or nurse.

The monitoring device does not require intra-vascular access. For long-term (weeks or months) cardiac monitoring, this offers previously unavailable data, ease of use, and enhanced safety compared to intra-vascular applications. The result is the ability to assess, at least qualitatively, the hemodynamic impact of heart rhythm disturbances in free-living individuals. Similarly, the monitoring device offers the potential to document heart rhythm and tissue blood flow surrogates (e.g., tissue impedance, temperature) during periods of hypotension of non-cardiac cause, thereby helping to assess the possibility of a cardiac and/or vascular cardiac etiology during diagnostic evaluation of patients. This portable diagnostic device is capable, without use of intra-cardiac electrodes, of diagnosing hemodynamic perturbations and ascertaining whether and to what degree they are caused by cardiac rhythm disturbances. At the same time, the device can be enhanced by adding non-vascular or intra-vascular leads for placing sensors at more distance sites in the body, or can be incorporated as a diagnostic element within a conventional cardiac pacemaker, ICD, or other implanted diagnostic instrument.

It is recognized that tissue blood flow may vary with respiration, posture, altered cardiac output, or changes in vascular tone. However, for patients in whom heart monitoring of the type discussed herein is selected (i.e., those with suspected arrhythmias or syncope), an abrupt substantial change in surrogate measures of blood flow may reasonably be expected to be due to an arrhythmia or other abrupt hypotensive state. Thus, detection of suspected flow alterations, along with ECG correlation, will assist physicians in distinguishing whether cardiac arrhythmias (i.e., abnormally slow or fast heart rates) are responsible for hypotensive symptoms or whether other mechanisms (e.g., vasodepressor hypotension without arrhythmia) are at fault. In many instances, hypotension occurs without evident arrhythmia. The present monitoring device is designed to detect this type of clinical problem in free-living individuals.

From the foregoing, it will be apparent to those skilled in the art that the present invention provides, in exemplary non-limiting embodiments, a wide variety of design options for the electrodes, sensors, leads, and the like for the monitoring device. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An implantable monitoring device comprising:
    a device body configured to be implanted subcutaneously into a patient;
    a plurality of impedance electrodes configured on or near the device body and for implantation into the patient with the device body, the plurality of impedance electrodes being configured to be positioned less than about 5 centimeters from an extra-cardiac artery or extra-cardiac tissue that pulsates in response to pulses in the extra-cardiac artery, the plurality of impedance electrodes adapted to inject a current across the extra-cardiac artery or extra-cardiac tissue and measure a resulting voltage across the extra-cardiac artery or extra-cardiac tissue to determine an extra-cardiac arterial electrical impedance measure across a path that traverses the extra-cardiac artery or extra-cardiac tissue, the extra-cardiac arterial electrical impedance measure being indicative of pressure in the extra-cardiac artery;
    a plurality of electrocardiographic, ECG, electrodes configured on or near the device body and for implantation into the patient with the device body, the plurality of ECG electrodes adapted to detect an ECG signal of the patient;
    a memory in operable communication with a processor programmed to store in the memory information from which a hypotension episode of the patient is identifiable and from which it is determinable whether an ECG signal accompanying an identified hypotension episode was normal during the identified hypotension episode, the information comprising both the extra-cardiac arterial electrical impedance measures and the accompanying ECG signal obtained over a period of time by, respectively, the plurality of impedance electrodes and the plurality of ECG electrodes, the processor being programmed to store the extra-cardiac arterial electrical impedance measures and the accompanying ECG signal for the period of time in a manner such that the extra-cardiac arterial electrical impedance measures and the accompanying ECG signal are correlated with one another in time, wherein the memory and the processor are each disposed within the device body; and
    a telemetry component disposed inside the body of the device, wherein the processor is programmed to control the telemetry component to transmit the stored and time correlated extra-cardiac arterial electrical impedance measures and the accompanying ECG signal for the period of time to a device external of the patient.

2. The implantable monitoring device of claim 1 wherein the impedance electrodes include two electrodes that are configured to be positioned such that the two electrodes are spaced from one another in a direction generally parallel to the artery.

3. The implantable monitoring device of claim 1 wherein the impedance electrodes include two electrodes that are configured to be positioned such that the two electrodes are spaced from one another in a direction generally transversely across the artery.

4. The implantable monitoring device of claim 1 further comprising a temperature sensor configured to measure local tissue temperature of a patient's body in a region adjacent the temperature sensor.

5. The implantable monitoring device of claim 1 further comprising a battery.

6. The implantable monitoring device of claim 1 further comprising a warning component to provide warning based on the stored information.

7. The implantable monitoring device of claim 1 wherein the impedance electrodes protrude from an outer surface of the body of the device.

8. The implantable monitoring device of claim 7 further comprising a set of one or more auxiliary leads for placing a set of one or more additional electrodes.

9. The implantable monitoring device of claim 1 wherein the processor is programmed to store data in memory based on instructions delineating criteria for data to be stored.

10. The implantable monitoring device of claim 1 wherein the memory has looping memory capability.

11. The implantable monitoring device of claim 1 wherein the processor is programmed to store in the memory data temporally proximate to an event based on information detected by the impedance electrodes or based on a telemetry instruction of patient-activated triggering of an external device.

12. The implantable monitoring device of claim 1 wherein the impedance electrodes are adapted to be positioned within the vascular system.

13. The implantable monitoring device of claim 1 wherein the plurality of impedance electrodes are configured to be positioned about 3-4 centimeters from the extra-cardiac artery or extra-cardiac tissue.

14. The implantable monitoring device of claim 1 wherein the extra-cardiac artery or extra-cardiac tissue with respect to which the plurality of impedance electrodes are configured to be positioned is distal of the major vessel of the aorta.

15. The implantable monitoring device of claim 14 wherein the extra-cardiac artery or extra-cardiac tissue with respect to which the plurality of impedance electrodes are configured to be positioned is a subclavian artery.

16. The implantable monitoring device of claim 1 wherein the extra-cardiac artery or extra-cardiac tissue with respect to which the plurality of impedance electrodes are configured to be positioned is a pectoralis muscle.

17. The implantable monitoring device of claim 16 wherein the plurality of impedance electrodes are configured to be positioned against the pectoralis muscle.

18. The implantable monitoring device of claim 1, wherein the ECG signal being normal is the ECG signal indicating a normal heart rhythm for the patient.

* * * * *

UNITED STATES PATENT AND TRADEMARK OFFICE
CERTIFICATE OF CORRECTION

PATENT NO. : 7,899,526 B2  
APPLICATION NO. : 11/127055  
DATED : March 1, 2011  
INVENTOR(S) : David G. Benditt et al.

Page 1 of 1

It is certified that error appears in the above-identified patent and that said Letters Patent is hereby corrected as shown below:

On the Title Page, Item (75), in "Inventors", line 2, delete "Robert F. Patterson" and insert -- Robert P. Patterson --, therefor.

Signed and Sealed this  
Twenty-seventh Day of September, 2011

David J. Kappos  
*Director of the United States Patent and Trademark Office*